United States Patent
Xie et al.

(10) Patent No.: US 10,779,807 B2
(45) Date of Patent: Sep. 22, 2020

(54) STEERABLE SHEATH TUBE AND METHOD FOR OCCLUDING ATRIAL SEPTAL DEFECT

(71) Applicant: Lifetech Scientific (Shenzhen) Co., Ltd., Shenzhen (CN)

(72) Inventors: Shaobo Xie, Shenzhen (CN); Gang Wang, Shenzhen (CN); Mingyang Cai, Shenzhen (CN); Kui Liu, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 1067 days.

(21) Appl. No.: 14/940,398

(22) Filed: Nov. 13, 2015

(65) Prior Publication Data

US 2017/0079630 A1    Mar. 23, 2017

(30) Foreign Application Priority Data

Sep. 22, 2015    (CN) .......................... 2015 1 0607330

(51) Int. Cl.
*A61B 17/00*    (2006.01)
*A61B 90/00*    (2016.01)
*A61B 34/20*    (2016.01)

(52) U.S. Cl.
CPC .................... *A61B 17/0057* (2013.01); *A61B 2017/00323* (2013.01); *A61B 2017/00575* (2013.01);
(Continued)

(58) Field of Classification Search
CPC ...... A61B 17/0057; A61B 2017/00323; A61B 2017/00575; A61B 2017/00606;
(Continued)

(56) References Cited

U.S. PATENT DOCUMENTS 4,586,923 A * 5/1986 Gould ............. A61M 25/09033
600/434
5,185,004 A * 2/1993 Lashinski ......... A61M 25/0136
600/434
(Continued)

FOREIGN PATENT DOCUMENTS

CN    2543656 Y    4/2003
CN    1733421 A    2/2006
(Continued)

OTHER PUBLICATIONS

Zhang, Sheathing canal that can be adjusted so as to be bent, Jan. 2013, Google Patents, pp. 1-9 (English Translation) (Year: 2013).*
(Continued)

*Primary Examiner* — Alexander J Orkin
(74) *Attorney, Agent, or Firm* — Raymond Sun

(57) ABSTRACT

A steerable sheath tube has a tubular body having a distal end, a traction wire; and a handle connected to the tubular body. The handle has a lateral branch tube that is coupled to the tubular body at an angle thereof, a slider positioned inside the lateral branch tube for translating movement therein, and a positioning member provided within the lateral branch tube and positioned further from the tubular body than from the slider. One end of the traction wire is fixed on the slider while the other end thereof is fixed at the distal end of the tubular body, and when the slider is moved to come into contact with the positioning member, the distal end of the tubular body is bent to a predetermined angle. A method for occluding an atrial septal defect includes the steps of delivering an occluder from a right internal jugular vein to an atrial septal defect by using the steerable sheath tube, and releasing the occluder to occlude the atrial septal defect.

8 Claims, 7 Drawing Sheets

(52) U.S. Cl.
CPC .............. *A61B 2017/00606* (2013.01); *A61B 2017/00623* (2013.01); *A61B 2017/00907* (2013.01); *A61B 2034/2063* (2016.02); *A61B 2090/378* (2016.02); *A61B 2090/3925* (2016.02)

(58) Field of Classification Search
CPC .......... A61B 2017/00623; A61B 2017/00907; A61B 2034/2063; A61B 2090/378; A61B 2090/3925; A61M 25/0105
USPC ........................................................ 606/213
See application file for complete search history.

(56) References Cited

U.S. PATENT DOCUMENTS

| | | | | |
|---|---|---|---|---|
| 5,327,906 | A * | 7/1994 | Fideler | A61M 25/0136 600/585 |
| 5,824,031 | A * | 10/1998 | Cookston | A61M 25/01 607/122 |
| 8,273,073 | B2 * | 9/2012 | Levine | A61M 25/008 604/528 |
| 2009/0137953 | A1 | 5/2009 | Fischer et al. | |
| 2012/0203169 | A1 * | 8/2012 | Tegg | B29C 65/02 604/95.04 |
| 2013/0317542 | A1 * | 11/2013 | Clark | A61B 17/0057 606/213 |
| 2016/0074625 | A1 * | 3/2016 | Furnish | A61M 25/0147 604/95.04 |

FOREIGN PATENT DOCUMENTS

| | | |
|---|---|---|
| CN | 102580225 A | 12/2011 |
| CN | 102580225 A | 7/2012 |
| CN | 103857353 A | 6/2014 |
| CN | 103877660 A | 6/2014 |
| CN | 103877663 A | 6/2014 |
| CN | 202070772 U | 6/2014 |
| CN | 104027880 A | 9/2014 |
| CN | 204364567 U | 6/2015 |
| CN | 205181963 U | 4/2016 |
| WO | WO2013117138 A1 * | 1/2013 ............ A61M 25/01 |

OTHER PUBLICATIONS

First Office Action for corresponding China Application No. 201510607330.1.
Second Office Action for corresponding China Application No. 201510607330.1.
Third Office Action dated Nov. 26, 2018 for corresponding China Application No. 201510607330.1.
Search Reports for corresponding China Application No. 201510607330.1.

* cited by examiner

STEERABLE SHEATH TUBE AND METHOD FOR OCCLUDING ATRIAL SEPTAL DEFECT

FIELD OF THE INVENTION

The present invention relates to the field of medical instruments, and in particular to a steerable sheath tube and a method for occluding an atrial septal defect by using the same.

BACKGROUND OF THE INVENTION

During minimally invasive interventional diagnosis and treatment surgery, a medical sheath tube is used for establishing a passage, conveying or withdrawing instruments, delivering drugs or exporting body fluid, and so on. In the design and manufacture of sheath tubes, generally, according to different intended applications of sheath tubes, distal ends of the sheath tubes are preformed into different curved shapes so as to fit for an anatomical shape of a particular diseased part, so that it is convenient to align the distal end of a sheath tube with the diseased part in the human body. Recently, distal-end-preformed interventional diagnosis sheath tubes of various shapes and angles have been successively developed and have been put into use clinically. These distal-end-preformed interventional diagnosis sheath tubes generally may accurately reach a diseased part by virtue of a guide wire and a dilator. Due to its flexibility, the guide wire may easily enter into the diseased part to establish a conveying passage. The preformed dilator is inserted into an inner cavity of a tube body. When the sheath tube and the dilator advance along the guide wire and then reach the diseased part, both the sheath tube and the dilator will be directed to a target position under the forced action of the guide wire. However, after the dilator and the guide wire are retracted from the sheath tube, the distal end of the sheath tube is unable to be maintained in the original preformed shape (i.e., being unable to reach a predetermined angle), so that the distal end of the sheath tube is deviated from the target position and the accurate release of an instrument at the target position is thus impacted.

In order to more accurately control the angle of bending of the distal end of a sheath tube, steerable sheath tubes are gradually concerned. However, a majority of steerable sheath tubes have a large range of angles of bending, but it is required to perform fine adjustment to a certain particular anatomical structure of the human body at a particular angle. Therefore, when such steerable sheath tubes are operated, an operator not only needs to take additional time to adjust the angle of bending of the distal end to a particular angle, but also needs to constantly pay attention to the scale on the steerable sheath tube to determine whether the distal end of the steerable sheath tube is adjusted to the particular angle, so that the operator cannot quickly and accurately adjust the angle of bending of the distal end of the sheath tube to a particular angle. As a result, the duration of operation is prolonged and the surgical risks to patients are increased.

SUMMARY OF THE INVENTION

The present invention provides a steerable sheath tube which may quickly and accurately allow the angle of bending of a distal end of the sheath tube to reach a predetermined angle, and a method for occluding an atrial septal defect by using the steerable sheath tube, in order to shorten the duration of operation and reduce the surgical risks to patients.

The steerable sheath tube of the present invention has a tubular body having a distal end, a traction wire; and a handle connected to the tubular body. The handle has a lateral branch tube that is coupled to the tubular body at an angle thereof, a slider positioned inside the lateral branch tube for translating movement therein, and a positioning member provided within the lateral branch tube and positioned further from the tubular body than from the slider. One end of the traction wire is fixed on the slider while the other end thereof is fixed at the distal end of the tubular body, and when the slider is moved to come into contact with the positioning member, the distal end of the tubular body is bent to a predetermined angle The present invention also provides a method for occluding an atrial septal defect, which includes the steps of delivering an occluder from a right internal jugular vein to an atrial septal defect by using the steerable sheath tube, and releasing the occluder to occlude the atrial septal defect.

Compared with the prior art, the present invention uses a positioning member to limit an endpoint of a translation region of the slider at the proximal end, so that a movable distance of the slider corresponds to the angle of bending of the distal end of the steerable sheath tube, and the angle of bending of the distal end of the steerable sheath tube may be adjusted to the predetermined angle as long as the slider is moved to come into contact with the positioning member during a surgical operation. Therefore, the steerable sheath tube provided by the present invention may quickly and accurately allow the angle of bending of the distal end of the sheath tube to reach the predetermined angle, at which the released occluder may be accurately aligned with the atrial septal defect part, so that it is convenient for the positioning and release of the occluder. Consequently, the duration of operation for occluding the atrial septal defect by using the steerable sheath tube is shortened, and the surgical risks to patients are reduced.

BRIEF DESCRIPTION OF THE DRAWINGS

The present invention will be further described below h reference to the accompanying drawings and embodiments, in which.

DETAILED DESCRIPTION OF THE EMBODIMENTS

To understand the technical features, objects and effects of the present invention more clearly, the specific implementations of the present invention will be described below in detail with reference to the accompanying drawings.

In the field of invasion medical treatment, the end of a device that is closer to an operator is defined as a proximal end, while the end farther away from the operator is defined as a distal end.

Figure 1:
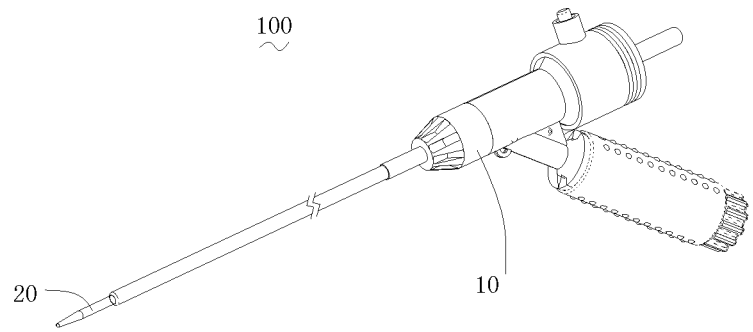
FIG. 1 is a schematic diagram of a steerable device according to an embodiment of the present invention.
Figure 2:
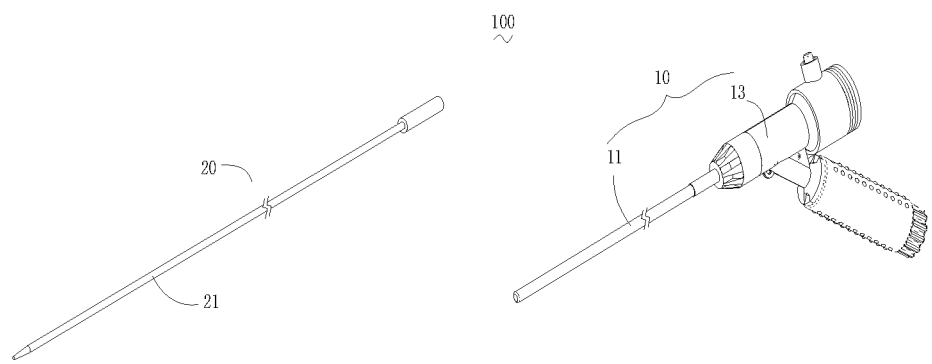
FIG. 2 is an exploded view of the steerable device of FIG. 1.
Figure 3:
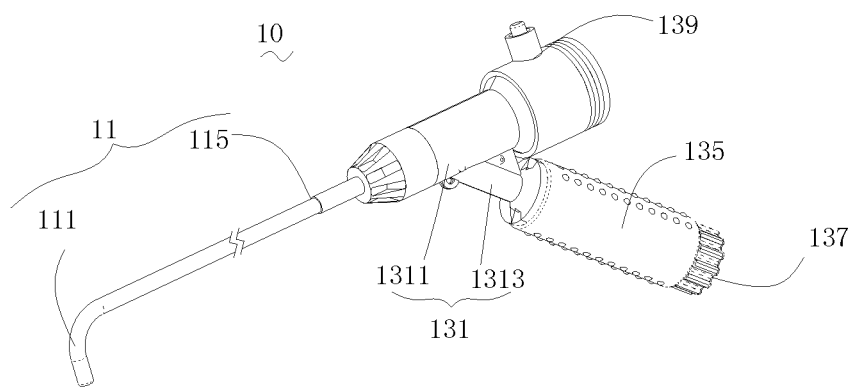
FIG. 3 is a schematic diagram of a steerable sheath tube of the steerable device of FIG. 1.
Figure 4:
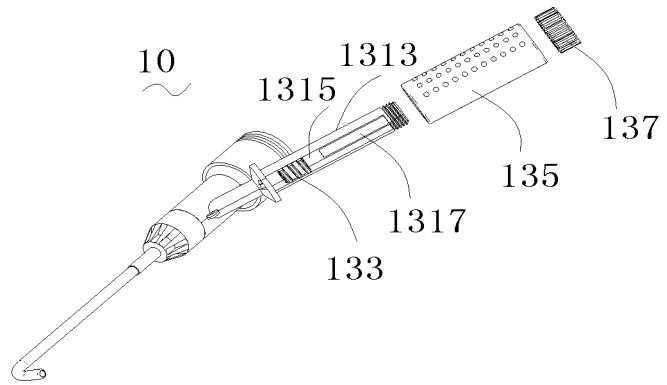
FIG. 4 is an exploded perspective view of assembly of the steerable sheath tube of FIG. 3.
Figure 5:
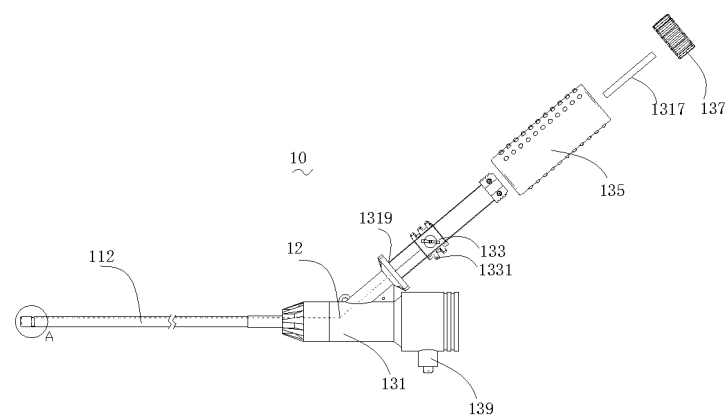
FIG. 5 is an exploded perspective view of the steerable sheath tube of FIG. 3 taken from another perspective.
Figure 6:
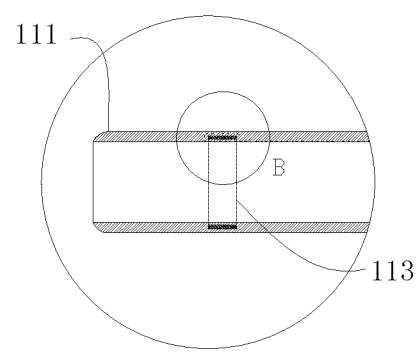
FIG. 6 is an enlarged cross-sectional view of the area A of FIG. 5.
Figure 7:
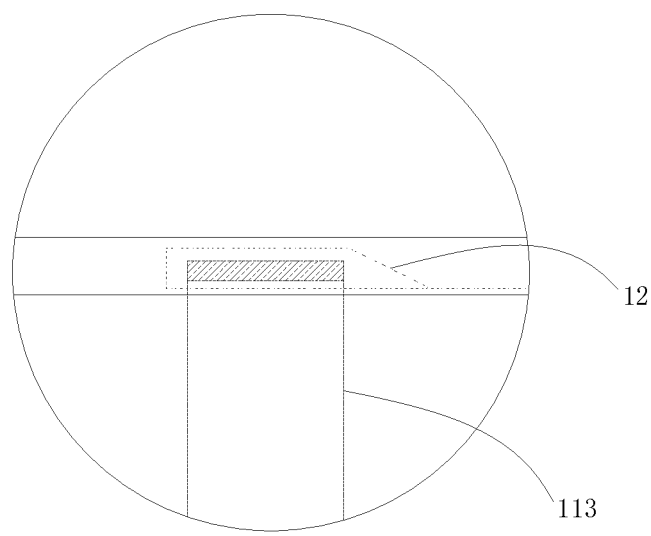
FIG. 7 is an enlarged view of the area B of FIG. 6.
Figure 8:
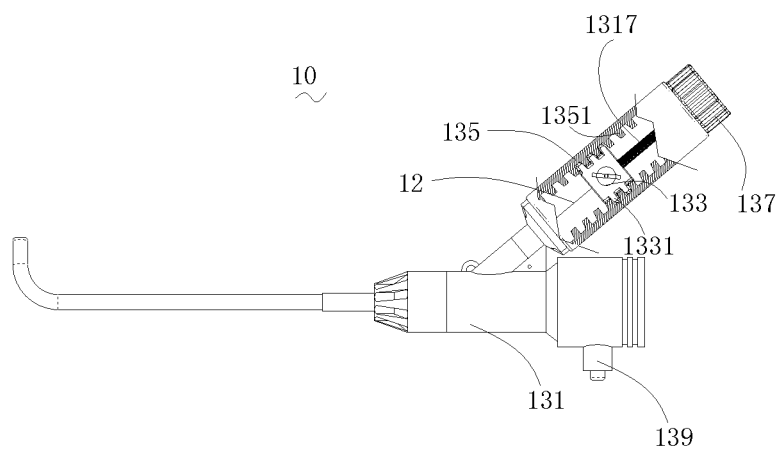
FIG. 8 is a partial cross-sectional view of the steerable sheath tube of FIG. 3.

Referring to FIG. 1 and FIG. 2, a steerable device 100 according to the present invention includes a steerable sheath tube 10 and a sheath core 20 accommodated within the steerable sheath tube 10.

Referring to FIGS. 3-8 together, the steerable sheath tube 10 includes a hollow tubular body 11, a traction wire 12 and a handle 13. The tubular body 11 has a flexible distal end 111 and a hard proximal end 115. The proximal end 115 is connected to the handle 13. The tubular body 11 further includes at least one conveying inner lumen 112 for conveying an instrument (for example, an atrial septal defect occluder, a ventricular septal defect occluder, etc.), a drug, or body fluid therethrough to a predetermined position. The traction wire 12 is accommodated within a wall of the tubular body 11 along an axial direction of the tubular body 11. One end of the traction wire 12 is provided within the wall of the distal end 111 and connected to an anchor ring 113 coaxial to the distal end 111, while the other end thereof is connected to the handle 13. By operating the handle 13, the traction wire 12 may drive the distal end 111 of the tubular body 11 to be adjusted to a predetermined angle by pulling the anchor ring 113. The predetermined angle is any angle from 0° to 180°.

The sheath core 20 is movably accommodated within the tubular body 11, and is provided within with an inner lumen 21 allowing a guide wire to pass therethrough and running through the proximal end and distal end of the sheath core 20. The distal end of the sheath core 20 extends out the distal end 111 of the tubular body 11 in order to prevent the distal end 111 of the tubular body 11 from scratching the vascular wall while moving within a blood vessel.

The handle 13 includes a Y-shaped connector 131, a slider 133, a rotary drum 135, an end cover 137 and a T-shaped connector 139. The Y-shaped connector 131 has a main branch tube 1311, and a lateral branch tube 1313 which is connected to the main branch tube 1311 and intersects the tubular body 11 at an angle.

The main branch tube 1311 is connected to the tubular body 11, and an inner lumen of the main branch tube 1311 communicates with the inner lumen 112 of the tubular body 11. The lateral branch tube 1313 extends from one side of the main branch tube 1311 and is communicated with the main branch tube 1311. The length of the lateral branch tube 1313 is about 5 cm to 10 cm, and the outer diameter of the lateral branch tube 1313 is about 0.5 cm to 1 cm. The angle between a longitudinal axis of the lumen of the main branch tube 1311 and a longitudinal axis of the lumen of the lateral branch tube 1313 ranges from 10° to 70°. Two opposing guide grooves 1315 each having a width of 0.2 cm to 0.5 cm are arranged along the longitudinal axis of the lateral branch tube 1313. Preferably, the length of each of the guide grooves 1315 is 30% to 90% of that of the lateral branch tube 1313, and the guide grooves 1315 are in an elongated shape. A preset positioning member 1317 is positioned within the lateral branch tube 1313, and is used for preventing the further bending of the distal end 111 of the tubular body 11 after the distal end 111 of the tubular body 11 is adjusted to the predetermined angle. In this embodiment, the positioning member 1317 is a positioning pin, one end of which is fixed at an end of the lateral branch tube 1313 far away from the tubular body 11 while an end face of the other end of which faces to the slider 133. In the present embodiment, the positioning member 1317 has a length of about 26 cm, and the predetermined angle is 90°. In other embodiments, the predetermined angle may be 180°, 60°, or 120°, among others. It should be understood that the predetermined angle may be varied as required, and the length of the positioning member 1317 may also be varied as required.

The slider 133 is disposed in the lateral branch tube 1313 and closer to the tubular body 11 than the positioning member 1317, and is able to translate along the longitudinal axis of the guide grooves 1315. One end of the slider 133 is connected to the proximal end of the traction wire 12 so that the moving slider 133 and traction wire 12 may drive the distal end 111 of the tubular body 11 to be adjusted to the predetermined angle. In this embodiment, referring to FIG. 4 to FIG. 5, the slider 133 is of a cuboid structure having a pair of parallel side faces of which are in contact with opposing inner walls of the lateral branch tube 1313 while another pair of parallel side faces of which are provided with teeth 1331, respectively. The teeth 1331 are protruded from the guide grooves 1315. The slider 133 may be made from metal (for example, stainless steel) or polymer material. The color of the slider 133 is different from the color of the lateral branch tube 1313, so that the slider 133 can be easily identified and seen by the clinician. The lateral branch tube 1313 may be made from light color (for example, white or light blue) material, while the slider 133 is made from deep color (for example, red, black or dark blue) material, for example, high-hardness plastics (POM, PA, ABS, etc.) and formed by machining or injection molding. In addition, a limiting disk 1319 may be provided at a base of the lateral branch tube 1313 close to the main branch tube 1311. As the inner diameter of the rotary drum 135 is less than the outer diameter of the limiting disk 1319, the limiting disk 1319 supports the rotary drum 135 to resist the tension of the traction wire when the rotary drum 135 is rotated, so that the stable free rotation of the rotary 135 is ensured.

The rotary drum 135 is a hollow cylinder having a length slightly greater than or equal to that of the guide grooves 11315, and may be sheathed on the lateral branch tube 1313 for free rotation and enclose the guide grooves 1315. Spiral tooth grooves 1351 matched with the teeth 1331 of the slider 133 are provided in an inner wall of the rotary drum 135. The rotating rotary drum 135 drives the slider 133 to do linear reciprocating motion to pull the traction wire 4 connected to the slider 133, so as to change the angle of bending of the distal end of the tubular body 1. The rotary drum 135 may be made from transparent material, for example, PC, PS, PET or other transparent plastics, so that the lateral branch tube 1313 may be seen through the rotary drum 135 and it is thus ensured that the slider 133 within the rotary 135 may be seen through the rotary drum 135 from different directions.

The end cover 137 is fixedly connected to a proximal end of the lateral branch tube 1313 far away from the main branch tube 1311 for the purpose of preventing the rotary drum 135 from being separated from the lateral branch tube 1313. In this embodiment, the end cover 137 is circular, and the outer diameter of the end cover 137 is greater than the inner diameter of the rotary drum 135. It should be understood that the end cover 137 may also be square, triangular, pentagonal, or any other shape as long as the diameter of a circumference of the end cover 137 is greater than the inner diameter of the rotary drum 135.

Optionally, the T-shaped connector 139 may be connected to a three-way valve (not shown) through a hose pipe. An annular cover is provided at the proximal end of the T-shaped connector 139. The three-way valve may be connected by an injector or other instruments in order to inject fluid into or extract fluid from the conveying inner lumen 112 of the tubular body 11.

In use, an operator is only required to rotate the rotary drum 135. Upon rotation of the rotary drum 135, the tooth grooves 1351 engage with the teeth 1331 of the slider 133. Due to the limitation of the guide grooves 1315, the slider 133 moves only along the axial direction of the rotary drum 135. The two ends of the rotary drum 135 are limited by the limiting disk 1319 and the end cover 137, respectively, and the tooth grooves 1351 are rotated along with the rotary drum 135 but is not able to be axially translated along the rotary drum 135. When the rotary drum 135 is rotated clockwise, the slider 133 is moved to the end cover 137 from the limiting disk 1319 and the tension of the traction wire 12 is increased, so that the angle of bending of the distal end of the tubular body 11 is forced to increase. After the slider 133 comes into contact with the positioning member 1317, the slider 133 is unable to be moved, that is, the operator is prompted that the distal end of the steerable sheath tube 10 has been adjusted to the predetermined angle. When the rotary drum 135 is rotated counterclockwise, the slider 133 is returned to the limiting disk 1319, the tension in the traction wire 12 is reduced, and the angle of bending of the distal end of the tubular body 11 is also reduced. When the slider 133 is controlled to return to the limiting disk 1319, the distal end 111 of the tubular body 11 is automatically returned to an initial natural state.

The present invention uses a positioning member 1317 to limit an endpoint of a translation region of the slider 133 at the proximal end, so that a movable distance of the slider 133 corresponds to the angle of bending of the distal end 111 of the steerable sheath and the angle of bending of the distal end 111 of the steerable sheath may be adjusted to the predetermined angle as long as the slider 133 is moved to come into contact with the positioning member 1317 during a surgical operation. Therefore, the steerable sheath tube 10 provided by the present invention may quickly and accurately allow the angle of bending the distal end 111 of the sheath tube 10 to reach a predetermined angle. The duration of operation is shortened, and the surgical risks to patients are reduced.

Those skilled in the art may understand that, after an operator adjusts the distal end of the steerable sheath tube 10 to a predetermined angle, the angle of the distal end 111 of the steerable sheath tube 10 may be finely adjusted as required, so that the angle of bending of the distal end 111 of the steerable sheath tube 10 is slightly less than the predetermined angle, thereby adapting to patients having different anatomical structures.

Figure 9:
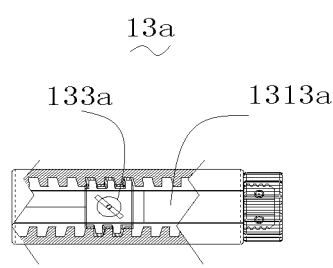
FIG. 9 is a schematic diagram of a handle of a steerable sheath tube according to another embodiment of the present invention.
Figure 10:
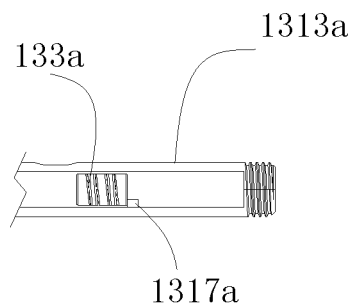
FIG. 10 is a schematic diagram of a lateral branch tube of the handle of FIG. 9.
Figure 11:
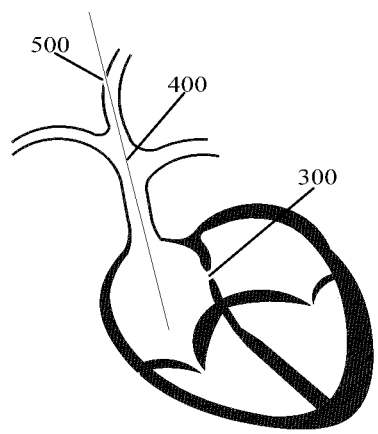
FIG. 11 is a schematic diagram of a human heart after puncturing a right internal jugular vein and delivering a guide wire into a right atrium.

Referring to FIG. 9 and FIG. 10, a handle 13a of a steerable sheath tube provided by a second embodiment of the present invention includes a lateral branch tube 1313a and a slider 133a accommodated within the lateral branch tube 1313a. The lateral branch tube 1313a is substantially the same as the lateral branch tube 1313, and a difference therebetween is that the positioning member 1317a of the lateral branch tube 1313a is a bump provided on an inner wall of the lateral branch tube 1313a.

Referring to FIGS. 11-20, a method for occluding an atrial septal defect 300 by using a steerable device 100 and an occluder is provided, including the following steps.

Step 1: A puncture passage 500 is formed at a right internal jugular vein of a neck (referring to FIG. 11). For example, during puncturing, the tip of a puncture needle forms an angle of 30 degrees with the skin, and the tip is pointed to the right papilla. Specifically, a conventional trachea cannula and general anesthesia are employed, and a transesophageal echocardiography probe is inserted. A patient lies on the back, his or her head is higher than his or her feet, the shoulder is supported, and the head is biased to the left and leaned back as far as possible. Carotid pulse is touched at the inner edge of sternocleidomastoid muscle, and the puncture needle is inserted at a position of about 0.5 cm from the outer edge of a pulsation point to form the puncture passage 500.

Step 2: A guide wire 400 is delivered into a right atrium from the puncture passage 500 through the right internal jugular vein. See FIG. 11.

Figure 12:
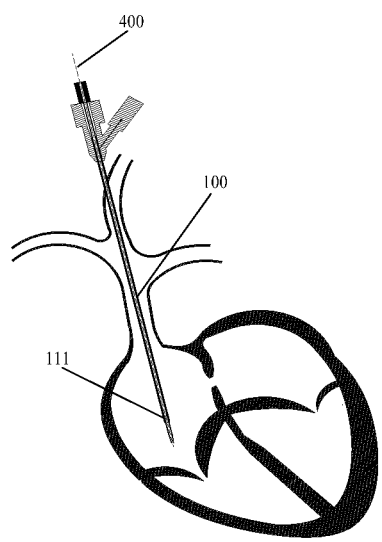
FIG. 12 is a schematic diagram from FIG. 11 after a proximal end of the steerable device is conveyed to the right atrium by the guide wire.
Figure 13:
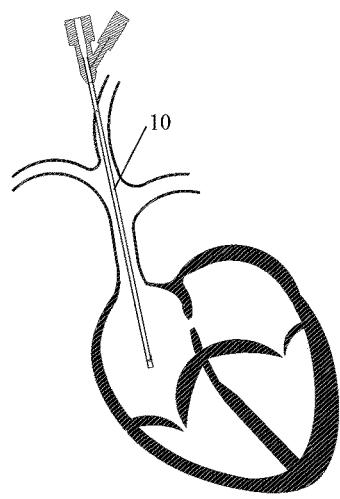
FIG. 13 is a schematic diagram from FIG. 12 showing the guide wire and a sheath core of the steerable device retracted from the steerable sheath tube.
Figure 14:
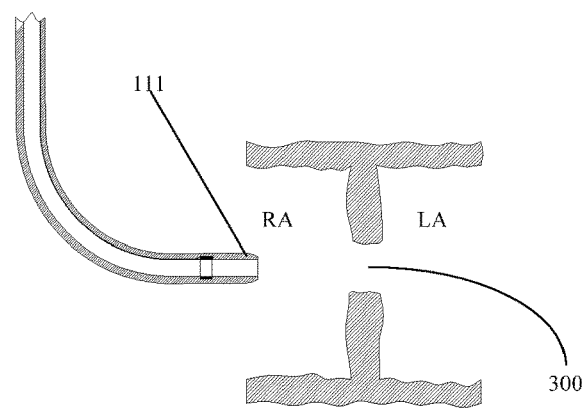
FIG. 14 is a schematic diagram from FIG. 13 after a distal end of the steerable sheath tube is bent to align with an atrial septal defect.
Figure 15:
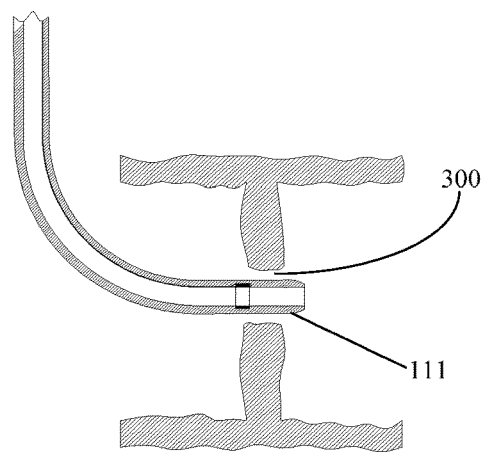
FIG. 15 is schematic diagram from FIG. 14 after the steerable sheath tube is adjusted to allow the distal end of the steerable sheath tube to be perpendicular to a plane of the atrial septal defect and positioned in the middle of the atrial septal defect.

Step 3: Referring to FIG. 12, a distal end of the steerable sheath tube device 100 is advanced to the right atrium under the guidance of the guide wire 400. Specifically, the distal end 111 of the steerable device 100 is advanced into the patient's body at a predetermined depth. The predetermined depth is approximately equal to a distance from a puncture point to the right papilla of the patient.

Step 4: Further referring to FIG. 13, a sheath core 20 and the guide wire 400 are removed from a tubular body 11 of the steerable sheath tube 10.

Step 5: Further referring to FIG. 14 and FIG. 15, the steerable sheath tube 10 is adjusted until the distal end 111 of the steerable sheath tube 10 is perpendicular to a plane of the atrial septal defect 300 and positioned in the middle of the atrial septal defect 300. Specifically, the handle 13 is operated first so that a central line of the distal end 111 of the steerable sheath tube 10 forms an angle of 90 degrees with a central axis of the proximal end of the tubular body 11. Next, the tubular body 11 of the steerable sheath tube 10 is rotated to allow the distal end 111 to align with the atrial septal defect 300. Then, the steerable sheath tube 10 is moved to allow the distal end 111 to pass through the atrial septal defect 300 at about 8 mm to 12 mm. Finally, the depth of the distal end 111 of the steerable sheath tube 10 into the human body is adjusted, and the handle 13 is operated such that the distal end 111 of the steerable sheath tube 10 is perpendicular to a plane of the atrial septal defect 300 and positioned in the middle of the atrial septal defect 300. In this embodiment, the distal end passes through the atrial septal defect 300 at about 10 mm.

Figure 16:
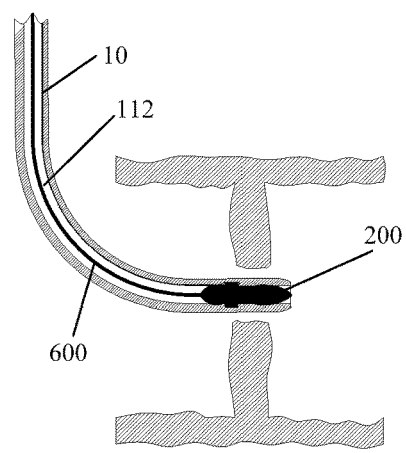
FIG. 16 is a schematic diagram from FIG. 15 after an occluder is conveyed to the atrial septal defect through the steerable sheath tube under the push of a delivery cable.

Step 6: Referring now to FIG. 16, an occluder 200, which is in a radially compressed state and connected to a delivery cable 600, is advanced to the atrial septal defect 300 through the conveying inner lumen 112 of the steerable sheath tube 10.

Figure 17:
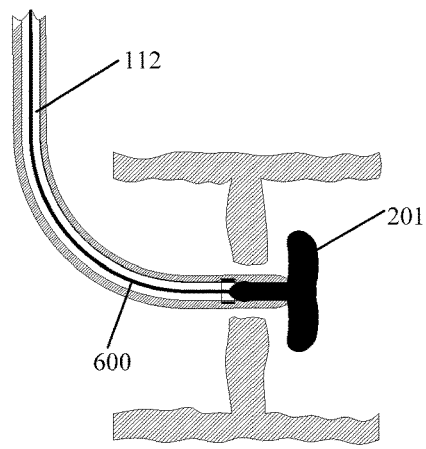
FIG. 17 is a schematic diagram from FIG. 16 after a left disk of the occluder is released.

Step 7: Referring now to FIG. 17, the occluder 200 is pushed out from the conveying inner lumen 112 to release a left disk 201 of the occluder 200.

Figure 18:
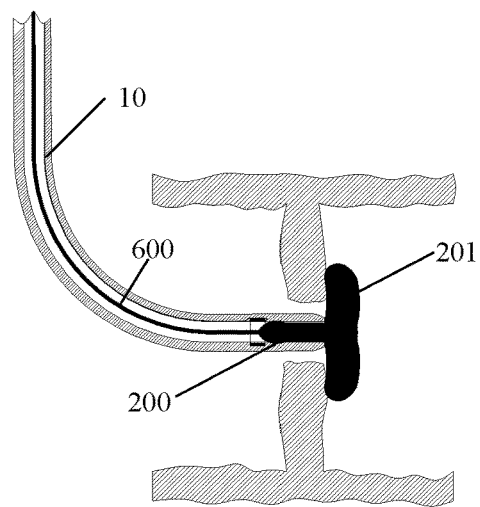
FIG. 18 is a schematic diagram from FIG. 17 after the steerable sheath tube and the delivery cable are retracted to allow the left disk to contact a wall of a left atrium.

Step 8: Referring now to FIG. 18, the occluder 200 and the steerable sheath tube 10 are retracted so that the left disk 201 is attached to a wall of a left atrium.

Figure 19:
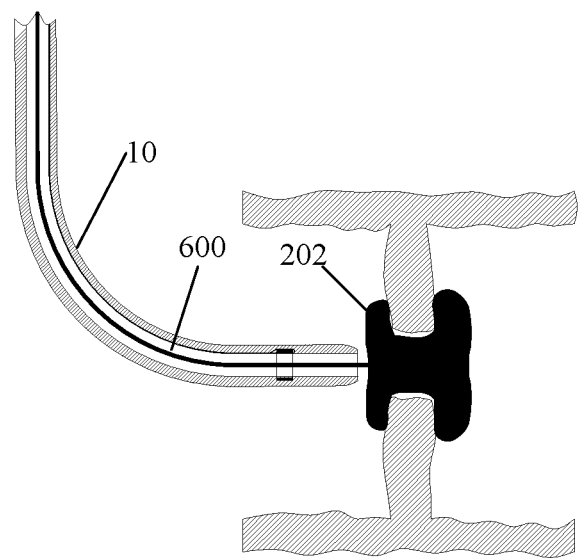
FIG. 19 is a schematic diagram from FIG. 18 after the steerable sheath tube is retracted to release a right disk of the occluder.

Step 9: Referring now to FIG. 19, the steerable sheath tube 10 is further retracted to release a right disk 202 of the occluder 200.

Figure 20:
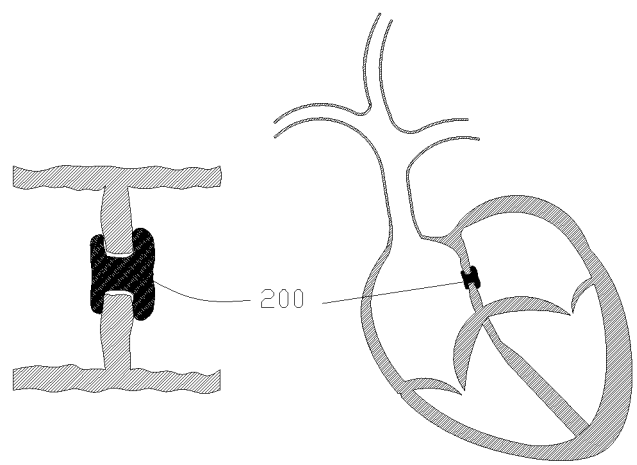
FIG. 20 is a schematic diagram illustrating how the occluder of FIG. 19 occludes the atrial septal defect.

Step 10: Referring now to FIG. 20, the delivery cable 600 and the occluder 200 are disconnected, and the steerable sheath tube 10 and the delivery cable 600 are retracted from the human body, so that the occlusion of the atrial septal defect 300 is completed with the occluder 200 occluding the atrial septal defect 300.

It is to be noted that steps 1 to 10 are all performed under the guidance of transesophageal ultrasound. Those skilled in the art should understand that steps 1 to 10 may also be performed under the guidance of chest ultrasound.

The method for occluding an atrial septal defect provided by the present invention has the following advantages: 1) the method allows a non-invasive treatment in that the patient's chest does not need to be opened, so that the procedure entails only a small risk; 2) the diameter of the internal jugular vein is greater than that of the femoral vein, so a steerable sheath tube 10 capable of delivering an occluder 200 having a larger diameter may be used; 3) the delivery path is shorter than that via the femoral vein, and accordingly, it is easy to operate; 4) the method of the present invention does not need a large scale X-ray device and so there is no radiation risks; 5) under the guidance of transesophageal ultrasound, the anatomical structure of the heart and the steerable sheath tube 10 may be shown clearly; 6) for a large atrial septal defect, the same effect as transthoracic occlusion may be achieved as the distal end 111 of the steerable sheath tube 10 is perpendicular to the plane of the atrial septal defect.

Although the embodiments of the present invention have been described with reference to the accompanying drawings, the present invention is not limited to the specific implementations. These specific implementations are merely illustrative but not restrictive. A person of ordinary skill in the art may make various forms under the teaching of the present invention without departing from the aim of the present invention and the protection scope of the appended claims, and those forms shall fall into the protection scope of the present invention.

The invention claimed is:

1. A steerable medical sheath tube, comprising:
a tubular body having a distal end;
a traction wire; and
a handle connected to the tubular body, the handle comprising a lateral branch tube that has a proximal end, and a distal end that is coupled to the tubular body at an angle thereof, a slider positioned inside the lateral branch tube for translating movement therein, and a positioning member provided within the lateral branch tube and positioned further from the tubular body than from the slider, wherein the positioning member is a pin, the pin having a longitudinal axis with a proximal end and a distal end along the longitudinal axis, with the proximal end fixed at the proximal end of the lateral branch tube, and the distal end abutting the slider;
wherein one end of the traction wire is fixed on the slider while the other end thereof is fixed at the distal end of the tubular body, so that movement of the slider adjusts the angle of the distal end of the tubular body, and wherein the positioning member limits an endpoint of a movable distance of the slider so that the movable distance of the slider corresponds to the angle of bending of the distal end of the tubular body.

2. The steerable sheath tube according to claim 1, wherein teeth are provided on both sides of the slider, and the handle further comprises:
a rotary drum which is sheathed on the lateral branch tube for rotation thereabout;
guide grooves extending along an axis of the lateral branch tube; and
wherein the slider translates its movement along the guide grooves, and a spiral tooth groove is provided on an inner wall of the rotary drum, and is aligned with the teeth of the slider.

3. The steerable sheath tube according to claim 2, wherein a limiting disk is provided at a base of the lateral branch tube adjacent to the tubular body, with the rotary drum having an inner diameter that is less than an outer diameter of the limiting disk.

4. The steerable sheath tube according to claim 2, wherein an end cover is provided at an end of the lateral branch tube away from the tubular body, and the end cover has an outer diameter that is larger than the inner diameter of the rotary drum.

5. The steerable sheath tube according to claim 2, wherein the length of the guide groove is 30% to 90% of the length of the lateral branch tube.

6. The steerable sheath tube according to claim 1, wherein the predetermined angle is any angle less than 180 degrees.

7. The steerable sheath tube according to claim 1, wherein the length of the lateral branch tube ranges from 5 cm to 10 cm, and the outer diameter of the lateral branch tube ranges from 0.5 cm to 1 cm.

8. The steerable sheath tube according to claim 1, wherein the handle further comprises a main branch tube communicating with a proximal end of the tubular body, and an included angle between an axis of a lumen of the main branch tube and an axis of a lumen of the lateral branch tube ranges from 10 degrees to 70 degrees.

* * * * *